(12) United States Patent
Wang (10) Patent No.: US 7,300,761 B2
(45) Date of Patent: Nov. 27, 2007

(54) METHODS AND DEVICE FOR DETECTING PROSTATE SPECIFIC ANTIGEN (PSA)

(76) Inventor: Tang J. Wang, 12671 Acacia Ter., Poway, CA (US) 92064

(*) Notice: Subject to any disclaimer, the term of this patent is extended or adjusted under 35 U.S.C. 154(b) by 450 days.

(21) Appl. No.: 10/851,253

(22) Filed: May 20, 2004

(65) Prior Publication Data

US 2004/0214254 A1    Oct. 28, 2004

Related U.S. Application Data

(62) Division of application No. 09/687,017, filed on Oct. 13, 2000, now Pat. No. 6,764,825.

(51) Int. Cl.
*G01N 33/533* (2006.01)
(52) U.S. Cl. .................. 435/7.1; 435/7.4; 435/7.5; 435/7.6; 435/7.9; 435/7.92; 435/7.93; 435/7.94; 435/975; 436/514; 436/518; 436/524; 436/810; 436/825
(58) Field of Classification Search .................. None
See application file for complete search history.

(56) References Cited

U.S. PATENT DOCUMENTS 5,075,078 A    12/1991  Osikowicz et al. ........... 422/56
5,120,643 A    6/1992   Ching et al. ................ 435/7.92
5,266,497 A    11/1993  Imai et al. ................... 436/514
5,395,754 A    3/1995   Lambotte et al. ......... 435/607.4
5,501,983 A    3/1996   Lilja et al.
5,521,102 A    5/1996   Boehringer et al.

(Continued)

FOREIGN PATENT DOCUMENTS

EP            653625        5/1995

(Continued)

OTHER PUBLICATIONS

Harvey et al., Guide to Diagnostic Rapid Test Device Components, (Jan. 2000). (Exhibit 16).

(Continued)

*Primary Examiner*—Bao-Thuy L. Nguyen
(74) *Attorney, Agent, or Firm*—Mandel & Adriano (57) ABSTRACT

An immunoassay device and assay to detect an antigen, such as PSA, in a biological sample. The device comprises a solid support having multiple reaction zones containing capture antibodies directed to the antigen. Exposure of a test sample to a mixture of incubation antibodies with known and different concentrations prior to exposure to the capture antibodies in the reaction zones facilitates determination of a range of concentrations of the antigen.

7 Claims, 4 Drawing Sheets

U.S. PATENT DOCUMENTS

| | | |
|---|---|---|
| 5,599,677 A | 2/1997 | Dowell et al. |
| 5,714,389 A | 2/1998 | Charlton et al. ............ 436/514 |
| 5,877,078 A | 3/1999 | Yanagida .................... 439/612 |
| 5,895,765 A | 4/1999 | Rheinheimer et al. ...... 436/514 |
| 5,968,839 A | 10/1999 | Blatt et al. |
| 5,989,921 A | 11/1999 | Charlton et al. ............ 436/501 |
| 6,001,658 A | 12/1999 | Fredrickson |
| 6,008,056 A | 12/1999 | Thieme ...................... 436/514 |
| 6,107,049 A | 8/2000 | Allard et al. |
| 6,248,597 B1 | 6/2001 | Eda et al. |

FOREIGN PATENT DOCUMENTS

| | | |
|---|---|---|
| EP | 653639 | 5/1995 |
| EP | 703454 | 3/1996 |
| EP | 656118 | 2/1997 |
| GB | 2204398 | 11/1988 |
| WO | 95/01128 | 1/1995 |
| WO | WO98/36278 | 8/1998 |

OTHER PUBLICATIONS

Qualisys Diagnostics, Inc. 510(k) Summary, Qualisys PSA Immunoassay, the author and publication date are currently unknown. (Exhibit 17).

Qualigen Incorporated 510(k) Summary, Qualigen Incorporated, the author and publication date are currently unknown. (Exhibit 18).

METHODS AND DEVICE FOR DETECTING PROSTATE SPECIFIC ANTIGEN (PSA)

This application is a Divisional application of U.S. Ser. No. 09/687,017 filed Oct. 13, 2000. now U.S. Pat. No. 6,764,825. The contents of all the foregoing applications are incorporated by reference in to the present application.

Throughout this application various publications are referenced. The disclosures of these publications are hereby incorporated by reference into this application in order to more fully describe the state of the art to which the invention pertains.

The present invention relates to a device and diagnostic methods for detecting an antigen, such as prostate specific antigen (PSA), in biological samples. More particularly the present invention provides a PSA immunoassay system in which a range of PSA concentrations in a sample is determined by adjusting the sensitivity of detection of various zones containing different PSA monoclonal antibodies in order to detect and monitor prostate cancer.

BACKGROUND OF THE INVENTION

The prostate specific antigen (PSA) is a glycoprotein of 28,700 Daltons, consisting of 237 amino acid residues mainly secreted by the prostate gland secretory luminar cells lining the secretory duct. (McCormack R T et al., *Urology* 45,729-744, 1995).

Small quantities of PSA are normally found in the circulatory system. The amount of serum PSA can increase as carcinomas of the prostate develop and mature. Elevated serum PSA levels have been used to aid in the diagnosis and monitoring of prostate cancer, for example, for the early detection of prostate adenocarcinoma. (Rittenhouse, H. G. et al., *Critical Reviews in Clinical Laboratory Sciences*, 35(4), 275-368, 1998).

As is conventionally understood or practiced in the field of urology, men having serum PSA concentrations less than 2 ng/ml generally are not diagnosed with, or considered to have, prostate cancer. However, when serum PSA concentration levels increase, the likelihood of being diagnosed with prostate cancer increases. For example, typically, one in nine men that have serum PSA concentration between 2 to 4 ng/ml will be diagnosed with prostate adenocarcinoma. When the concentration of serum PSA is between 4 and 10 ng/ml, one in four men will be diagnosed with prostate cancer, and when the levels increase above 10 ng/ml, the ratio is one out of two men. (Catalona, W. J. et al., *Journal of the American Medical Association*, 274(15), 1214-1220, 1995; Catalona, W. J. et al., *J. Urol.*, 151, 1283-1290, 1994; Brawer, M. K. et al., *J. Urol.*, 147, 841-845, 1992; Oesterling, J. F., *J. Urol.*, 145, 907-923, 1991).

Existing immunoassay systems used to detect or monitor prostate cancer incorporate one or more monoclonal antibodies (mAbs) capable of binding to any of the six different known major PSA epitopes (see Stenman U. H. et al. *Tumor Biology*, 20, suppl. 1, 1-12, 1999).

Generally, immunoassays can be categorized into quantitative or qualitative groups, as discussed below. The quantitative type of immunoassay is typically more expensive and relatively difficult to conduct. The qualitative immunoassays are relatively less expensive and easier to perform, but do not necessarily provide the amount or accuracy of information obtained with the quantitative immunoassays.

With respect to the quantitative type of immunoassays, conventionally known as "sandwich assays" and as conventionally practiced, one antibody is coupled to a solid support, and a second antibody is coupled to a detectable label. A test antigen having separate binding sites (epitopes) for the first and second antibodies is exposed to the antibody coupled to the solid support such that the antigen binds to that antibody. Subsequently, the labeled second antibody is added to the support to permit the binding of the labeled second antibody to the test antigen. Thus, the amount of the antigen present in a sample is a function of the amount of detected label bound to the second antibody bound to the antigen. Examples of such detectable labels include chromophores, radioisotopes, or enzymes which can be converted into a product that can be measured photometrically. When the amount of detected label is compared to the amount of antibody binding in a standard sample containing known amounts of antigen, quantitative results can be obtained. However, as indicated above, this procedure is typically complicated, time consuming, and expensive to perform compared to immuno-chromatography techniques described below, because this assay requires personnel training, complicated instruments, and test samples or standards, to be used during each measurement or assay.

To attempt to reduce the difficulty and expense of the quantitative immunoassay described above, immuno-chromatography methods have been developed. These tests provide qualitative information (e.g. a positive or negative result). The immuno-chromatography method typically utilizes a solid support such as a membrane strip having a region (a "reaction zone") coated with a first antibody (a "capture antibody") that is capable of binding to an antigen. The concentration of the capture antibody is empirically determined prior to the manufacture of the device. The concentration of the capture antibody is typically selected based on antibody/antigen binding data corresponding to the detection of an antigen above a single selected concentration threshold. The concentration threshold (i.e., the concentration of antigen that is believed to correlate with a disease condition) is chosen based on clinical or research data used in the diagnosis and/or monitoring of diseases having disease specific antigens. As discussed herein, clinicians typically begin to carefully monitor male patients for prostate cancer when their serum PSA levels are greater than 2 ng/ml. Thus, existing immuno-chromatography assays utilize a concentration of the capture antibody in the reaction zone that permits detection of PSA above a 2 ng/ml concentration threshold. A second antibody (a "detection antibody"), capable of binding the antigen at a different site, or epitope, from the first antibody, is usually coupled with color particles, such as colloidal gold or blue latex, and is applied in a solution having other factors, such as detergents, to facilitate solubilization of the labeled antibody onto a different region (a "reagent zone") of the solid support, e.g., near one end of the membrane strip. The sample is then loaded on the membrane near the end that contains the detection antibody. The sample subsequently diffuses through the region with the detection antibody where the antigen binds to the detection antibody, and diffluses continuously toward the region of the capture antibody. Because the detection antibody is applied to the reagent zone with solution components that increase solubilization of the antibody, the detection antibody is capable of diffusing with the antigen as it diffuses towards the other end of the membrane strip. When the antigen bound by the detection antibody interacts with the capture antibody, it is trapped in the reaction zone. If the test antigen present in the solution does not recognize the capture antibody, or it is present at a concentration lower than the concentration threshold determined by the capture antibody, the test antigen coupled with the detection antibody with the color particles will not bind to the membrane strip region containing the capture antibody, and thus, no staining will be present in the reaction zone, indicating that the antigen is present at a concentration less than the concentration threshold of the capture antibody (i.e. 2 ng/ml). Similarly, if no antigen is present in the sample, no binding will occur with either of the antibodies, and thus, no staining will occur. Therefore, a positive result is indicated by the presence of color in the reaction zone. The intensity of color correlates with the amount of bound antigen in the reaction zone. Thus, it is possible that the user will be able to make a more quantitative interpretation based on the degree of staining intensity.

However, as indicated above, these known immunochromatography-based PSA antibody assays only provide information of PSA concentration above a single value, or concentration threshold, for example 2 ng/ml, based on the clinical values discussed above, and do not provide multiple values or concentration thresholds, in a single test, to facilitate more accurate measurement of PSA concentration in a single test.

Thus, there remains a need for a simple, rapid, and affordable assay that provides more accurate measurements of antigens, such as PSA, in a sample, and overcomes the shortcomings of the prior known devices and methods above.

SUMMARY OF INVENTION

Accordingly, the present invention provides a device and assay methods for detecting and determining ranges of concentration of an antigen, such as PSA, present in a biological sample.

In one embodiment, the device comprises serially located zones including a first reaction zone which has been coated with a predetermined amount of a first capture antibody that will bind against a first epitope of an antigen; a second reaction zone which has been coupled with a predetermined amount of a second capture antibody that will bind against a second epitope of the antigen after binding in the first reaction zone; and an incubation zone, or "reagent zone", containing a predetermined amount of first and second incubation antibodies that are the same type as the first and second capture antibodies, and a third detection antibody bound to a detectable label, the third antibody capable of binding to a third epitope of the antigen.

Additional reaction zones with additional capture antibodies recognizing and binding different antigen epitopes can also be provided. Relatedly, each additional capture antibody is also present as an incubation antibody in the reagent zone. The reaction zones are configured to provide sequential exposure of the test antigen in the biological sample to the capture antibodies in the reaction zones.

The present invention provides a method for detecting an antigen in a biological sample. The preferred method includes exposing an antigen, such as PSA, in a biological sample to a predetermined quantity of incubation antibodies capable of recognizing and binding specific epitopes of the antigen, at least one of the epitope-specific antibodies being coupled with a detectable label. Subsequently, the solution containing the antibodies and antigen is sequentially exposed to reaction zones on a solid support, each reaction zone containing capture antibodies at predetermined concentrations reactive with distinct epitopes of the antigen and of the same type as the incubation antibodies.

DETAILED DESCRIPTION OF THE INVENTION

Definitions

As used herein, a "reaction zone" is defined as a region on the solid support of the device of the invention containing predetermined concentrations of capture antibodies, preferably monoclonal antibodies, attached to the solid support, each capture antibody capable of recognizing and binding a distinct epitope of a test antigen. As discussed herein, the reaction zone can be any designated region or portion of a membrane strip, or it can be in a container such as a test tube, or it can consist of a well in a microtiter plate. The reaction zone provides a specific location for detecting the presence and range of concentration of an antigen in a biological sample.

As used herein, a "reagent zone" is defined as a region of the device of the invention containing a mixture of incubation antibodies that are identical in type to the capture antibodies in the reaction zone, and a detection antibody. The reagent zone is preferably provided on the device of the invention as a designated region or portion of a membrane strip. Alternatively, the reagent zone is separate from the solid support containing the reaction zones for example, in a container such as a test tube or as a well in a microtiter plate. A test antigen in a sample is exposed to the reagent zone prior to being exposed to any reaction zone. The reagent zone is typically formed using an incubation solution containing incubation antibodies and other reagents, such as inert proteins and non-ionic detergent, to solubilize the test antigen and antibodies, and to reduce non-specific binding of the test antigen and antibodies.

As used herein, a "capture antibody" is defined as an antibody, preferably a monoclonal antibody, attached to the solid support of the device of the invention in a reaction zone. Each capture antibody is selected to recognize and bind a particular, distinct epitope of the test antigen at a predetermined concentration, and is identical in type to an incubation antibody in the reagent zone.

As used herein, an "incubation antibody" is defined as an antibody, preferably a monoclonal antibody, identical in type, but not necessarily concentration, to a capture antibody, that is present at a predetermined concentration in the reagent zone. The concentrations of incubation antibodies are predetermined before performing the assay of the invention by conducting titration experiments with known quantities of the test antigen, and are selected based on the detection of a test antigen at or above a concentration threshold as described above. For example, based on clinical or research data, if a clinically significant concentration threshold is determined to be 4 ng/ml, the concentration of one incubation antibody is chosen, based on titration experiments and data, to detect a concentration of test antigen at or above 4 ng/ml in a reaction zone.

As used herein, a "detection antibody" is defined as an antibody, preferably a monoclonal antibody, that recognizes and binds the test antigen at a binding site or epitope distinct from that of the incubation and capture antibodies. The detection antibody is coupled to a detectable label such as a chromophore, enzyme, radioisotope, or colored particle, such as colloidal gold or color latex. Examples of enzymes include, but are not limited to, alkaline phosphatase, beta galactosidase, or horseradish peroxidase which produce color when incubated with the appropriate substrate. The concentration of detection antibody to use in the device of the invention is predetermined by conducting experiments to determine amounts of detection antibodies that are needed to provide a detectable signal.

It will be understood by persons skilled in the art that a sufficient concentration of detection antibody is provided to ensure binding of the detection antibody to all, or essentially all, of the test antigen molecules. In other words, it is preferable to use as much detection antibody as possible without increasing non-specific binding of the detection antibody in the assay to improve the signal-to-noise ratio of the device of the invention.

As indicated above, the capture, incubation, and detection antibodies are preferably monoclonal antibodies (Kohler and Milstein, *Nature*, 256:495-97 (1975)), but one or more of the antibodies can be a polyclonal antibody, or fragment thereof, made by known methods (see, e.g., Rouseaux et al., "Optimal Conditions For The Preparation of Proteolytic Fragments From Monoclonal IgG of Different Rat IgG Subclasses", in Methods Enzymol., 121:663-69 (Academic Press 1986)).

As used herein, "range of concentration of an antigen" is defined as the range of antigen concentration values between the antigen concentration thresholds or limits defined in each reaction zone. "Concentration threshold" is defined as the concentration where an antigen is believed to correlate with a certain disease state based on data values obtained empirically, for example in clinical or research settings, for diagnosing and monitoring diseases having disease specific antigens that can bind to antibodies. For example, for purposes of this disclosure, the PSA concentration thresholds are 2, 4, and 10 ng/ml. These are PSA concentrations that have been shown to have clinical relevance in the diagnosis and monitoring of prostate cancer.

As described throughout the specification, certain specifications of the assay and device of the invention are determined prior to the manufacture and use of the device of the invention. For example, the components of the incubation solution and their concentrations (e.g., the concentrations of incubation and detection antibodies) in the reagent zone; the experimental conditions of the assay, such as buffer solution, pH, ionic strength, temperature, incubation times, solid phase support; the coupling chemistry between the support and the various antibodies, and the coupling chemistry between the detection antibody and the label, are preferably predetermined by conducting conventional experiments to optimize the performance of the device of the invention within the desired limits described herein.

Figure 1:
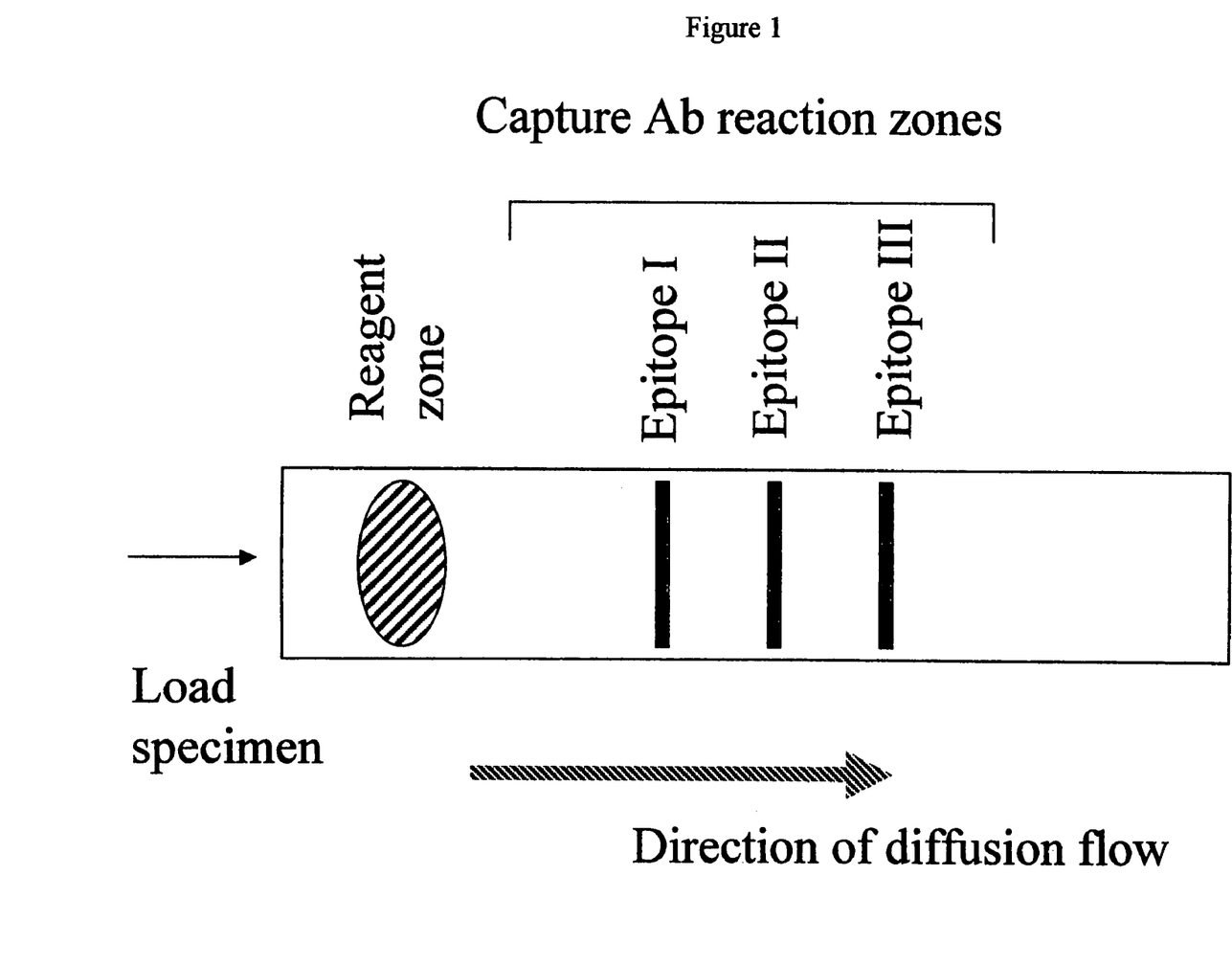
FIG. 1 illustrates a membrane strip as the solid support of the device of the invention containing three capture antibody reaction zones and one incubation antibody reagent zone.

Referring to FIG. 1, and to one exemplary embodiment of the invention for detecting PSA antigen, the device comprises a solid support, such as a membrane strip, having a plurality of sequentially arranged reaction zones, and preferably, at least one reagent zone. The membrane strip may be made of synthetic or natural materials, such as polystyrene, nylon, nitrocellulose membrane, or filter paper. The reaction zones contain monoclonal capture antibodies that bind distinct epitopes of a PSA antigen molecule. The solid support permits a solution containing the antigen being assayed to be transferred to each of the reaction zones by difflusion, or by physical means, such as pipetting. Other suitable solid supports include, but are not limited to, microtiter plates (see FIG. 2), chromatographic membranes, or other immunoassay devices such as silica chips (Affmatrix, Palo Alto, Calif.). As shown in FIG. 1, the PSA epitope I capture antibody is attached at the first reaction zone, the PSA epitope II capture antibody is attached at the second reaction zone, and the PSA epitope III capture antibody is attached at the third reaction zone. In one embodiment of the invention, the concentration of each capture antibody is identical for each reaction zone, i.e. the concentration of PSA epitope I capture antibody (for example, 10 µg/ml) is equal to the concentration of PSA epitope II capture antibody (for example, 10 µg/ml) which is equal to the concentration of PSA epitope III capture antibody (for example, 10 µg/ml). However, in other embodiments, the concentrations of capture antibodies can vary so long as they exceed the concentration of the test antigen so that the test antigen molecules will not bind to all of the capture antibody molecules. In that regard, typical antigen concentrations in biological samples are in the nanogram to low microgram range (e.g. 1 ng/ml-1 µg/ml) so that the capture antibody concentrations are in the low to high microgram range (e.g. 1-100 µg/ml). A minimum concentration of capture antibody is empirically selected (based on expected antigen concentrations) as discussed herein, to permit binding of all, or essentially all, of the test antigen that is available in the sample (i.e., all, or essentially all, of the test antigen that is not already bound to the incubation antibody that corresponds to the capture antibody in that reaction zone) applied to the device to the capture antibody zone, but not to permit saturation of the capture antibody by the test antigen. The capture antibodies are attached to the membrane strip, for example, by physical attachment as a result of the "stickiness" of the antibodies, or by chemical reaction coupling, so that they will not become soluble and detach when the membrane strip becomes wet. In other words, the capture antibodies can be understood to generally form a solid phase in the reaction zones.

Figure 2:
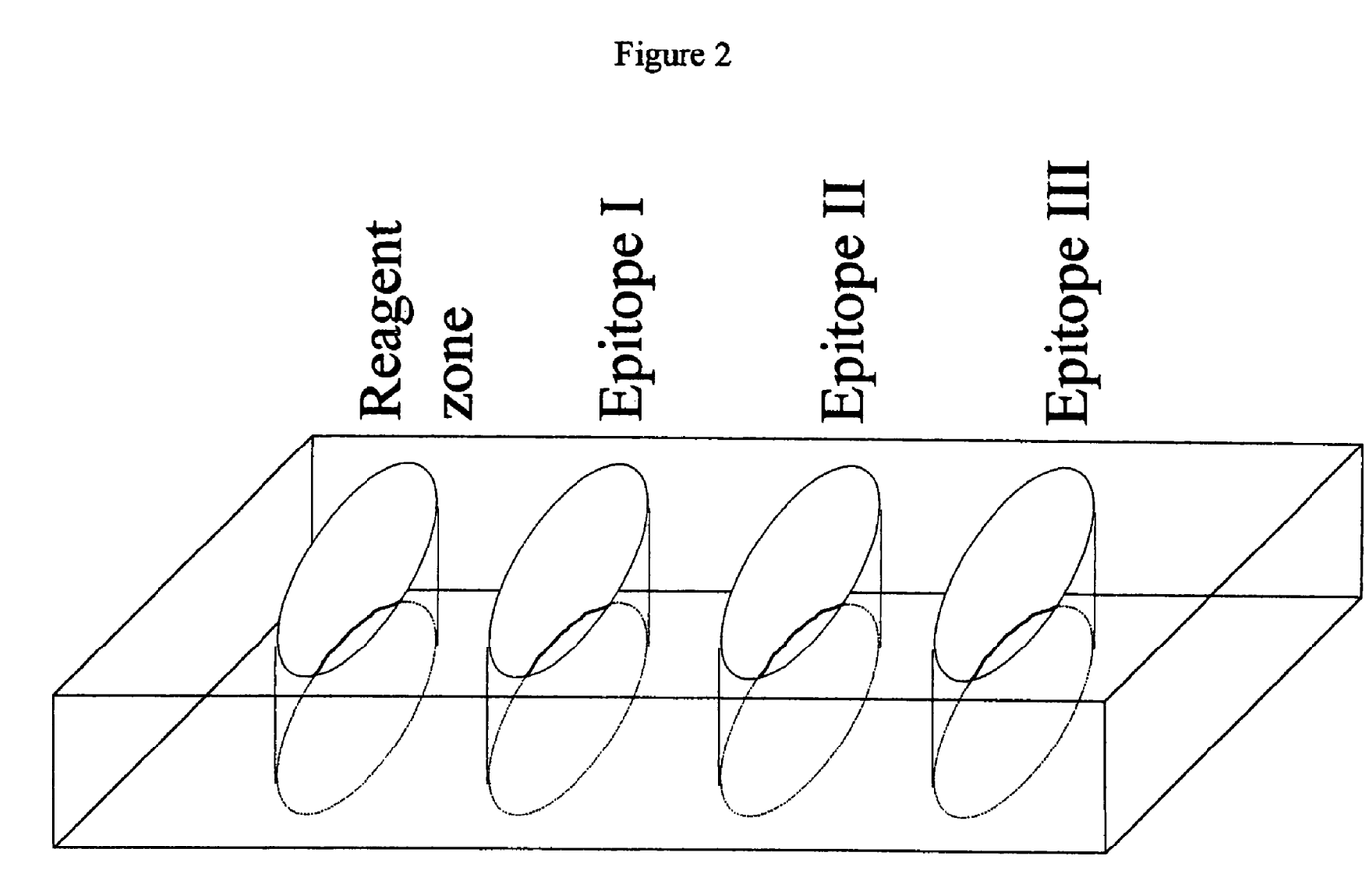
FIG. 2 illustrates a microtiter plate containing three reaction zones and one reagent zone in the device of the invention.

In the case where the invention is practiced with test tubes or microtiter plates as the solid support, such as is illustrated in FIG. 2, paramagnetic particles may be used to facilitate the attachment of capture antibodies to the reaction zones or wells of the microtiter plates. Various types of paramagnetic particles having different surface chemistry exist and are well known and used in the art (e.g., see U.S. Pat. Nos. 5,283,079 and 5,320,944). The particular type of particle selected will depend on the antigen and the experimental conditions in which the device of the invention is being used. Some examples of paramagnetic particles commonly used in instrument immunoassays can be found in systems such as Beckman Access (Fullerton, Calif.) and Bayer Immuno I (Tarrytown, N.Y.). Selection of the paramagnetic particle is determined empirically for the particular test antigen.

In the embodiment illustrated in FIG. 1, the membrane strip also includes a reagent zone, containing adhered or bound incubation antibodies that are the same type as the capture antibodies, and also bind PSA epitopes I, II, and III; and a detection antibody that binds another PSA epitope, such as PSA epitope V. The incubation solution used to form the reagent zone also contains inert proteins, such as bovine serum albumin (BSA); and a non-ionic detergent, such as Tween-20®. In addition, the incubation solution can include other components, such as casein, gelatin, nonfat dry milk, ovalbumin, polyvinyl pyrrolidone, polyvinyl alcohol, or animal serum components including bovine IgG, murine IgG, and goat IgG, to improve the usability and performance of the device of the invention. The particular components, in addition to the incubation and detection antibodies, used in the incubation solution and their concentrations vary depending on the antigen being tested and the experimental conditions of the assay. The components are preferably chosen based on results of empirical test experiments. The components are selected to optimize the results obtained with the device of the invention, for example, components are preferably chosen to increase the intensity and contrast of antigen specific staining, and minimize background staining, thereby optimizing the signal to noise ratio of the device of the invention. The incubation solution is prepared by mixing the foregoing components in a buffer solution, such as phosphate buffered saline (PBS). The reagent zone is generated by placing a volume (e.g., 10 µl) of the incubation solution onto the membrane strip near one end, and allowing the incubation solution to dry for transport and/or storage before use. Due to the presence of reagents, such as the inert proteins and Tween-20, the incubation and detection antibodies become soluble to facilitate diffusion of the antibody/antigen complexes to the sequentially arranged reaction zones as the membrane becomes wet during the course of the assay.

In one embodiment, the relative concentrations of the incubation antibodies in the reagent zone are related to the sequence of the capture antibodies in the reaction zones. By way of example, and in reference to FIG. 1 with three capture antibodies, because the PSA epitope I capture antibody (10 µg/ml) is in the first reaction zone (i.e., the test antigen/incubation solution will be exposed to that reaction zone before the second or third reaction zones), the concentration of the PSA epitope I incubation antibody (for example, 30 ng/ml) is greater than the concentration of the other incubation antibodies in the reagent zone. Because the PSA epitope II capture antibody (e.g., 10 µg/ml) is in the second reaction zone, the concentration of the PSA epitope II incubation antibody (for example, 15 ng/ml) is less than the concentration of the PSA epitope I incubation antibody (30 ng/ml) in the reagent zone, but is greater than the concentration of the PSA epitope III incubation antibody (for example, 7 ng/ml) in the reagent zone. Likewise, because the PSA epitope III capture antibody (e.g., 10 µg/ml) is in the third reaction zone, the concentration of the PSA epitope III incubation antibody (7 ng/ml) is less than the concentration of both the PSA epitope I and epitope II incubation antibodies in the reagent zone. Thus, the concentrations of the incubation antibodies in the reagent zone can be understood to be in a descending relationship based on the sequence of exposure of the test antigen to the reagent zones' capture antibodies. However, the concentration relationship can vary. For example, the concentration relationship in the reagent zone can be reversed so that the PSA epitope III incubation antibody has the highest concentration, and PSA epitope I incubation antibody has the lowest concentration. Alternatively, the PSA epitope I incubation antibody could have a concentration between the PSA epitope II and epitope III incubation antibody concentrations. The particular concentration relationship of the incubation antibodies will determine the staining pattern of the device of the invention.

As should be apparent from the foregoing description, the particular relationship of incubation antibody concentrations can vary depending on the particular embodiment of the device of the invention (i.e., the test antigen and antibodies selected).

Figure 4A:
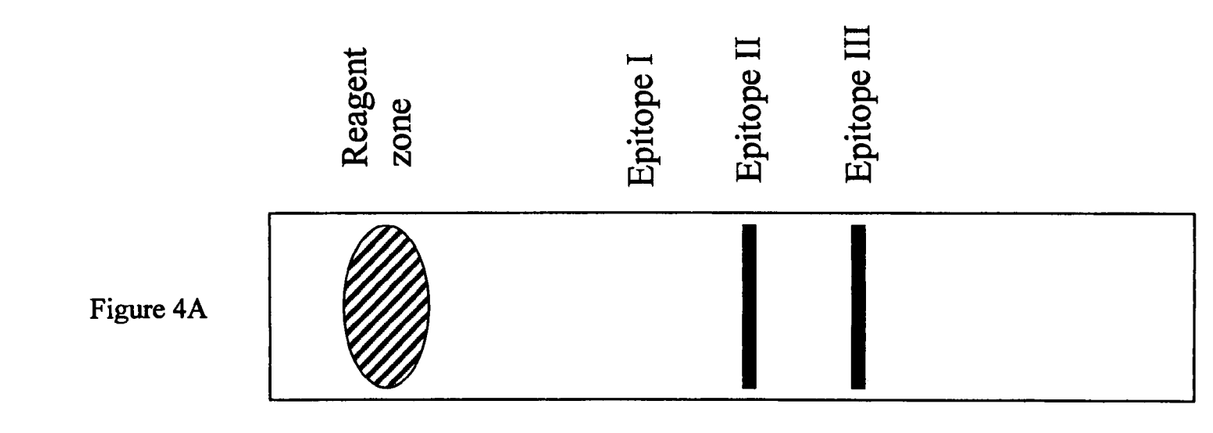
FIGS. 4A-4C illustrate examples of staining patterns that may be obtained using a device containing three capture antibody reaction zones, and one reagent zone with the methods of the invention.
Figure 4B:
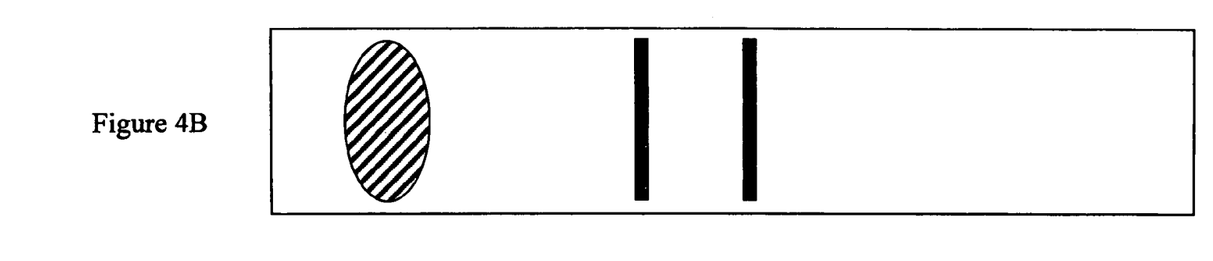
Figure 4C:
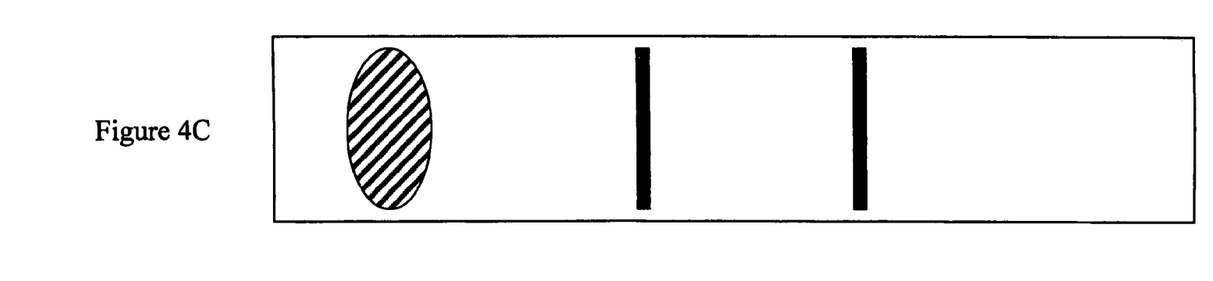

By way of example, and referring to FIG. 4A and the preceding example, if the concentrations of incubation antibodies are in a descending relationship with the concentration of PSA epitope I incubation antibody (30 ng/ml) being greater than the concentration of PSA epitope II incubation antibody (15 ng/ml), which is greater than the concentration of PSA epitope III incubation antibody (7 ng/ml), and the sequence of capture antibodies in the reaction zones is, the antibody to epitope I, the antibody to epitope II, and the antibody to epitope III, a signal produced in the epitope II and epitope III capture antibody reaction zones will indicate that the test antigen concentration is between 10 and 4 ng/ml, based on the results of titration experiments for the incubation antibodies as discussed below. Likewise, referring to FIG. 4B, if the concentration of PSA epitope I incubation antibody (7 ng/ml) is less than the concentration of PSA epitope II incubation antibody (15 ng/ml) which is less than the concentration of PSA epitope III incubation antibody (30 ng/ml), a biological sample having a PSA concentration between 4 and 10 ng/ml would cause positive staining in the epitope I and epitope II capture antibody reaction zones. Furthermore, as illustrated in FIG. 4C, if the concentration of the epitope I incubation antibody (15 ng/ml) is between the concentration of the epitope II (30 ng/ml) and epitope III (7 ng/ml) incubation antibodies, a test antigen having a concentration between 4 and 10 ng/ml will show positive staining in the epitope I and epitope III capture antibody reaction zones.

Signal will only be present in the reaction zones as compared to the rest of the membrane strip, because the presence of the inert protein component and non-ionic detergent in the incubation solution maintain the solubility of the incubation and detection antibodies so that as the assay is conducted, the incubation and detection antibodies are washed from the membrane strip where the antigen has not bound to the capture antibodies.

In designing the device of the invention, it is preferable to predetermine the preferred concentrations of the detection antibody, the capture antibodies, and the incubation antibodies for the particular antigen of interest before manufacturing the device. Persons of ordinary skill in the art will appreciate that the particular concentrations can vary depending on the antigen being tested, and that the following description can be applicable to any antigen for which binding antibodies are known or can be prepared using known methods in the art (see, e.g. Kohler and Milstein, *Nature*, 256:495-97 (1975)).

As indicated elsewhere herein, the concentration of the detection antibody is preferably selected so that all, or essentially all, of the test antigen molecules are bound by the detection antibody. Thus, the detection antibody can be provided at concentrations at least an order of magnitude greater than the expected concentration of the test antigen. For example, if a test antigen has an expected concentration of 10 ng/ml, the detection antibody concentration in the reagent zone (or incubation solution) can be 2,000 ng/ml (2 µg/ml). As discussed in the Examples herein, the polyclonal detection antibody (i.e. goat anti-PSA polyclonal antibody) is used at a concentration of 2 µg/ml for test PSA antigen concentrations ranging from 1 to 25 ng/ml. One method of determining a minimum concentration of detection antibody is to expose various known concentrations of the detection antibody (e.g., 100 ng/ml, 1 µg/ml, 5 µg/ml, and 10 µg/ml) to a predetermined concentration of test antigen (e.g., 20 ng/ml). The label bound to the detection antibody is detected, and the concentration of detection antibody (e.g., 2 µg/ml) that sufficiently yields a detectable signal is chosen as the concentration to be used in practicing the invention. The concentration of the detection antibody is then used to determine the concentrations of the capture antibodies and incubation antibodies as described below. These reactions can take place in test tubes, wells of microtiter plates, or other similar devices as are conventionally used in the art.

Once the concentration of detection antibody is determined, it is possible to measure a signal when the antigen binds to the capture antibody and thus determine the concentration of the capture antibodies to be used to practice the invention. Similar to the detection antibody, each capture antibody is preferably provided in a sufficient concentration to permit binding of all, or essentially all, of the corresponding epitopes on the test antigen molecules present in a biological sample. For example, if a sample is expected to have 1 ng/ml of the test antigen, the concentration of the capture antibodies in each reaction zone can be 1 µg/ml (e.g., at least one order of magnitude greater). An example of a method to determine the concentration of a capture antibody to be used is to attach preselected concentrations (e.g., 10 ng/ml, 100 ng/ml, 1 µg/ml, 10 µg/ml, and 100 µg/ml) of one type of a capture antibody to different reaction zones of a substrate, such as wells of a microtiter plate. Then, a preselected concentration of a test antigen (e.g. 20 ng/ml) prebound to a detection antibody (e.g., 2 µg/ml) is incubated in each reaction zone to permit sufficient binding to the capture antibody. As indicated above, the particular time for incubation of the labeled test antigen to the capture antibody is empirically determined based on the particular experimental conditions. The amount of signal produced, e.g., staining, is then measured visually or with a photometric plate reader, and the lowest concentration of capture antibody that yielded maximum staining is used in the device of the invention, and in the titration experiments described below. For example, if 10 ng/ml of capture antibody yielded a relative grade of staining of +1, 100 ng/ml yielded a relative grade of +2, 1 µg/ml of capture antibody yielded a relative grade of +3, 10 µg/ml of capture antibody yielded a relative grade of +4, and 100 µg/ml of capture antibody also yielded a relative grade of +4, the capture antibody is used at a concentration of 10 µg/ml because this is the lowest concentration of capture antibody resulting in the highest intensity of stain. In this example, "relative grade" is defined as the amount of staining in a given zone compared to the other zones (for example, an alternate grading scale could be "light staining intensity", "medium staining intensity", "dark staining intensity", and "very dark staining intensity"). The particular grade of staining is subjectively determined by comparison with the staining in the other zones.

The concentrations of incubation antibodies for a particular antigen are determined by titration experiments that are performed before preparing the assay for the test antigen. Referring to the embodiment of the invention wherein the test antigen is PSA, examples of titration experiments to determine the concentration of incubation antibodies needed to permit detection of the test antigen at particular antigen concentration thresholds or cut-off values for each of the reaction zones, are described in the Examples and FIG. 3, herein. In short, by using known concentrations of the antigen, such as PSA (e.g. 1, 2, 4, 10, and 25 ng/ml) by using commercially available PSA, and known concentrations of the various incubation antibodies (e.g. 15, 30, or 60 ng/ml), it is possible to determine the minimum amount of antigen detected by a particular concentration of a capture antibody (e.g. 10 µg/ml). For example, and as discussed in detail in the Examples, preincubation of a sample containing (1, 2, 4, 10, or 25 ng/ml) PSA with 15 ng/ml of PSA epitope I incubation antibody, and subsequently exposing the PSA/ epitope I incubation antibody solution to a reaction zone containing 10 µg/ml of the PSA epitope I capture antibody, results in the detection (e.g., staining that is two standard deviations above the background staining) of PSA concentrations above 4 ng/ml. Incubation of PSA with 30 ng/ml of PSA epitope I incubation antibody, and subsequently exposing the PSA/epitope I incubation antibody solution to a reaction zone containing 10 µg/ml of the PSA epitope I capture antibody, results in the detection of PSA concentrations above 10 ng/ml. These results indicate that 15 ng/ml of PSA epitope I antibody binds all, or almost all, the PSA epitope I binding sites when the PSA concentration is less than 4 ng/ml. As one would expect, the results also indicate that 30 ng/ml of PSA epitope I antibody binds all, or almost all, of the PSA epitope I binding sites when the PSA concentrations are less than 10 ng/ml. Thus, an incubation solution having 30 ng/ml of PSA epitope I antibody will bind all of the PSA epitope I binding sites for PSA concentrations less than 10 ng/ml, and consequently, no binding or staining will occur in the first reaction zone containing the PSA epitope I capture antibodies. Therefore, to detect a concentration of PSA greater than 10 ng/ml (e.g., the concentration threshold of the first reaction zone) in a sample, the incubation solution should contain 30 ng/ml of the PSA epitope I incubation antibody; similarly, to detect PSA concentrations greater than 4 ng/ml, the incubation solution should contain 15 ng/ml of the PSA epitope I incubation antibody.

In carrying out the method of the invention for detecting antigen in a sample, a portion of the sample is incubated in the reagent zone prior to exposure to a reaction zone. After incubation for a sufficient time to bind the incubation and detection antibodies to the test antigen, the sample is transferred to a first reaction zone, where the capture antibody present in the first reaction zone can bind to empty epitope sites on the antigen remaining after binding of the corresponding incubation antibodies present in the reagent zone.

After incubating the sample in the first reaction zone for a sufficient time to permit binding of the antigen to the first capture antibody (e.g., four hours), the sample is transferred to the second reaction zone. Those of ordinary skill in the art will understand that the incubation times can vary depending on a number of factors including the temperature at which the incubation occurs, the concentrations of the test antigen in the sample and incubation and detection antibodies in the reagent zone, and the kinetics of the various binding reactions.

These steps are repeated until the sample has been exposed to each of the reaction zones provided on the solid support of the device of the invention. Once the assay is complete, the results are visualized or measured by the formation of the signal (e.g., a color stain) from the label coupled with the detection antibody.

In cases where the detection antibody is bound to an enzyme label, the bound PSA in the reaction zones is detected using conventional immunological techniques. The presence of signal can be read visually and/or quantified by a photometric plate reader. Because the reaction zones represent various concentration threshold values of significant concentration thresholds of the test antigen, a range of test antigen concentrations can be determined using multiple positive or labeled (i.e., colored) reaction zones. In addition, the intensity of the label of the positive reaction zones can be used to further estimate the test antigen concentration within a given range. In one embodiment, signal intensity greater than 2 times the standard deviation of the nonspecific background signal of the microtiter plate is interpreted as a positive response. Nonspecific binding is determined by testing a sample without PSA in a similar manner described herein.

As indicated above, the foregoing description is illustrative of particular embodiments of the invention, and the specific structure, use, and numerical values therein are not to be construed as limiting the invention. In that regard, the invention can be useful in detecting any antigen in a biological sample, and may further aid in the diagnosis and monitoring of any condition, including diseases of the prostate and heart, such as cancer, having disease-specific antigens that can be measured using antibodies that bind to the antigens.

Additional zones on the support may enhance quantitative aspects of the assay provided by the device. For example, an additional zone can be used as a control to verify that the antigen is actually present within the biological sample. If a control zone is provided with the device of the invention, and no staining is present after the assay is performed, the user would assume either that the antigen was not present in the sample, or that it was at a concentration below the detection limit of the device. For example, a polyclonal antibody against the antigen is attached to the control zone to detect the presence of the test antigen at any concentration within the detection limit of the device, to validate the presence of the test antigen in the sample, and confirm the positive response of the reaction zones. Polyclonal antibodies are typically used as "controls" for detecting a test antigen due to their lower degree of specificity compared to monoclonal antibodies. As will be understood by persons skilled in the art, the detection limit of the device refers to the minimum concentration of antigen in a sample detectable by the device of the invention. This is determined empirically for the antigen of interest, if not otherwise known.

Additional reaction zones may be provided with the device of the invention so long as the additional capture and incubation antibodies added do not present steric interference with binding of any other antibody in any of the other assay zones. The potential limitation of the number of epitopes available for simultaneous antibody binding is a function of the physical size of antigen relative to the bound antibodies. Fragments of antibodies such as F(ab')2 or Fab of 100,000 daltons or 50,000 daltons may also be used in these zones. Methods of preparing antibody fragments are well known (see, e.g., Rouseaux et al., "Optimal Conditions For The Preparation of Proteolytic Fragments From Monoclonal IgG of Different Rat IgG Subclasses", in Methods Enzymol., 121:663-69 (Academic Press 1986)).

Advantages of the Invention

The subject invention overcomes the problems and shortcomings associated with current devices and methodologies of antigen screening, in particular for detection of PSA.

Among other things, the invention provides a device that does not require complicated, time consuming, and expensive instrumentation to perform and determine the results of the assay, or require training and hiring operators to use such equipment.

In addition, the invention provides more information than a simple positive or negative result conducted in a single test as is obtained with conventional immuno-chromatography devices. In that regard, the invention permits the testing of more than five concentrations of PSA (PSA has six distinct epitopes; one epitope is used for recognition by the detection antibody).

Furthermore, the invention eliminates the need for separate calibration of antigen standards that commonly accompanies known methods of antigen detection using either manual- or instrument-based immunoassay systems.

The subject invention will likely result in improved disease detection and monitoring than existing immunochromatography assays incorporating single concentration thresholds because the user of the invention will be able to quickly determine a subject's sample's PSA concentration within statistically and clinically significant ranges.

The following examples are presented to illustrate the experiments to precalibrate the device for the antigen of interest. The methodology and results will vary depending on the antigen being tested. The examples are not intended in any way to otherwise limit the scope of the invention.

EXAMPLE 1

This example provides a control to demonstrate that PSA is present within the sample being tested by the device and methods of the invention.

A microtiter plate (Immulon 4, Dynex, Franklin, MA) was coated with rabbit anti-PSA polyclonal antibody (Dako, Carpenteria, Calif.) at 50 µg/ml in PBS for 24 hours at 4° C. The plate was incubated with 1% bovine serum albumin (BSA) in PBS/0.1% Tween-20. Various concentrations of PSA (25, 10, 4, 2, or 1 ng/ml) (Scripps Lab, San Diego, Calif.) in 0.1% BSA in PBS/Tween-20 (50 µl) were added to the plate and incubated for 1 hour. The plate was washed with PBS/0.1% Tween-20, and 50 µl of goat anti-PSA polyclonal antibody (the detection antibody; Scripps Lab) at 2 µg/ml in 0.1% BSA/PBS/0.1% Tween-20 was added and incubated for one hour. The rabbit anti-goat Ig horseradish peroxidase (1:5000, Jackson Immuno Research, West Grove, Pa.) in the same buffer was added for one hour and the plate was washed. The orthophenylene diamine (OPD) substrate was added for 30 minutes and stopped with 4N $H_2SO_4$. The response was determined spectro-photometrically with a Spectra Max 340 (Molecular Devices, Sunnyvale, Calif.).

Positive staining (i.e. a spectral reading of at least 1) was present in each well. Thus, this experiment provides the conditions that can be used to provide a control zone in the device of the invention.

EXAMPLE 2

This example demonstrates the sensitivity of a reaction zone of the assay, (i.e. the lower limit of detection of the test antigen in that zone) without the use of the reagent zone, on the solid support of the device of the invention. In addition, it provides a control absorbancy curve to use as a basis to compare the results of the titration experiment described in Example 3.

A microtiter plate was coated with epitope I PSA monoclonal antibody at 10 µg/ml in PBS for 24 hours at 4° C. The plate was incubated with 1% BSA in PBS/0.1% Tween-20 for 1 hour. Various concentrations (25, 10, 4, 2, or 1 ng/ml) of PSA (50 μl) were added for 2 hours. Goat anti-PSA (2 μg/ml) was added for 2 hours. The plate was washed and rabbit anti-goat Ig horseradish peroxidase (1:5000) was added for 2 hours. The plate was washed again and OPD substrate was added for 30 minutes and stopped with 4N $H_2SO_4$. The response was measured photometrically with the Spectra Max 340 (Molecular Devices).

Figure 3:
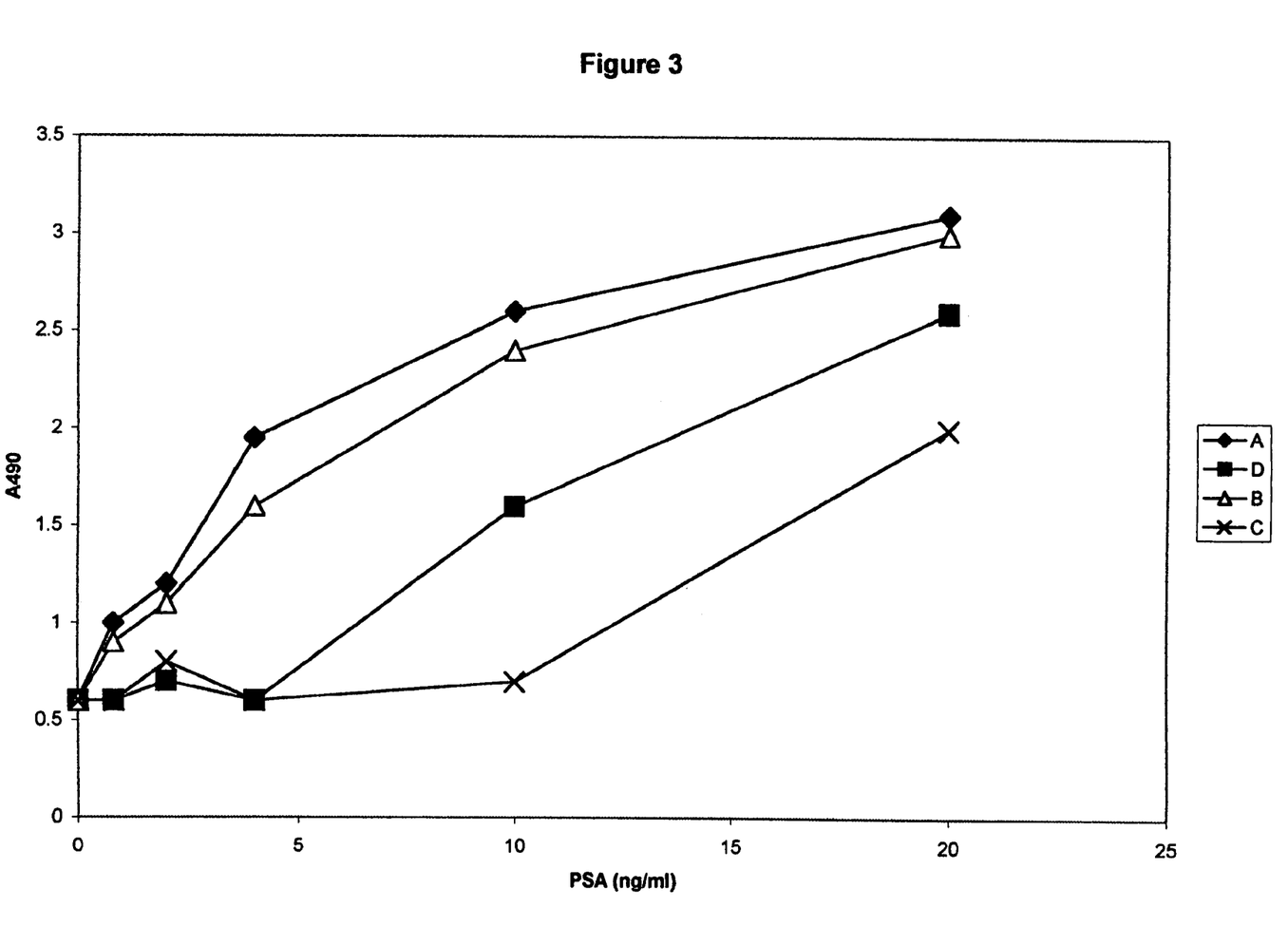
FIG. 3 is a graph showing the results of photometric analysis of PSA concentration for PSA bound to various concentrations of capture antibodies, as described in Examples 2-4, infra.

The results are illustrated in FIG. 3(A). PSA at concentrations as low as 2 ng/ml was detectable with a spectral reading of approximately 1. This data indicates the assay of the invention with a reaction zone containing 10 μg/ml of the PSA epitope I monoclonal antibody can detect PSA concentrations in biological samples as low as 2 ng/ml.

EXAMPLE 3

This example shows the ability of the invention to determine the concentration threshold of an antigen by initially exposing a sample containing a known amount of PSA to a reagent zone mixture having a known concentration of an incubation antibody to epitope I of PSA. In this example, two concentrations (15 and 30 ng/ml) of PSA epitope I incubation antibody are separately tested, and result in two distinct PSA concentration thresholds (4 and 10 ng/ml, respectively). These data are used to determine the concentration of incubation antibody to be used in the reagent zone (or well) of the device of the invention.

One microtiter plate reaction zone (or well) was coated with the epitope I PSA monoclonal antibody at 10 μg/ml in PBS for 24 hour at 4° C. The plate was then incubated with 1% BSA in PBS/1.0% Tween-20 for 1 hour. In the reagent zone, epitope I PSA mAb at 30 ng/ml or 15 ng/ml was added to various concentrations of PSA (25, 10, 4, 2, or 1 ng/ml) and incubated for 4 hours. The incubation solution was transferred to the microtiter plate reaction zone and incubated for 4 hours. The plate was washed, and goat anti-PSA at 2 μg/ml was added and incubated for 4 hours. The plate was washed and rabbit anti-goat Ig horseradish peroxidase (1:5000) was added for overnight at 4° C. followed by addition of OPD substrate for 30 minutes. The response was measured photometrically with the Spectra Max 340 (Molecular Devices).

The results of this experiment are illustrated in FIG. 3, for the two concentrations of the PSA epitope I incubation antibody, designated by the letters C (30 ng/ml epitope I antibody), and D (15 ng/ml epitope I antibody). When 30 ng/ml of the incubation antibody to epitope I was used in the reagent zone, PSA concentrations greater than 10 ng/ml were detectable in the first reaction zone having a PSA epitope I antibody concentration of 10 μg/ml. When 15 ng/ml of the incubation antibody to epitope I was used in the reagent zone, PSA concentrations greater than 4 ng/ml were detectable in the first reaction zone.

Based on these results, a reagent zone having an epitope I PSA mAb concentration of 15 ng/ml would permit detection of PSA in a biological sample at a concentration as low as 4 ng/ml. Similarly, if the reagent zone had an epitope I PSA mAb concentration of 30 ng/ml, PSA concentrations as low as 10 ng/ml could be detected. As discussed above, these values are used to determine the concentration thresholds for each of the reaction zones of the invention. Thus, to make a reaction zone containing PSA epitope I capture antibody have a concentration threshold of 4 ng/ml, the reagent zone includes 15 ng/ml of PSA epitope I incubation antibody.

EXAMPLE 4

Example 4 demonstrates the specificity and noninterference of the binding of the epitope I and epitope II incubation and capture antibodies to PSA antigen.

A microtiter plate was coated with epitope I PSA monoclonal antibody at 10 μg/ml in PBS for 24 hours at 4° C. The plate was incubated with 1% BSA in PBS/0.1% Tween-20 for 1 hour. Fifty microliters of epitope II PSA mAb (60 ng/ml) were added to various concentrations of PSA (25, 10, 4, 2, or 1 ng/ml) and incubated for 4 hours. The mixture was transferred to a microtiter plate and incubated for 4 hours. The plate was washed and goat anti-PSA at 2 μg/ml was added, and incubated for 4 hours. The plate was washed and rabbit anti-goat Ig horseradish peroxidase (1:5000) was added overnight at 4° C. followed by OPD substrate development for 30 minutes. The response was measured photometrically with the Spectra Max 340 (Molecular Devices).

Results of this experiment are illustrated in FIG. 3(B). When 60 ng/ml of the antibody to epitope II were used, PSA was detectable above 2 ng/ml.

Thus, referring to Example 2 and FIG. 3, a reagent zone mixture with epitope II PSA incubation antibody at a concentration of 60 ng/ml does not interfere with the binding of PSA by the PSA epitope I monoclonal capture antibody alone. In other words, and as illustrated by the data in FIG. 3, PSA in a sample could be detected at concentrations as low as 2 ng/ml when the sample was only exposed to a microtiter plate containing 10 μg/ml of PSA epitope I monoclonal capture antibody, and when the sample was exposed to 60 ng/ml of PSA epitope II monoclonal incubation antibody prior to exposure to the microtiter plate containing 10 μg/ml of PSA epitope I monoclonal capture antibody.

EXAMPLE 5

The purpose of this experiment is to further demonstrate the ability of the invention to determine an antigen concentration threshold for a reaction zone by initially exposing known amounts of PSA in a sample to a reagent zone solution having a known concentration of incubation antibody reactive with PSA epitope I and a known concentration of incubation antibody reactive with PSA epitope II. In addition, it demonstrates the lack of interference in binding of the antigen to incubation and capture antibodies that recognize different PSA epitopes. These data are then used to select the concentration of incubation antibodies to be used in the reagent zone.

Individual wells of a microtiter plate were coated with epitope I PSA monoclonal antibody (corresponding to the first reaction zone) or epitope II PSA mAb (corresponding to the second reaction zone) at 10 μg/ml in PBS for 24 hours at 4° C. The plate was incubated with 1% BSA in PBS/0.1% Tween-20 for 1 hour. Fifty microliters of epitope I PSA mAb (15 ng/ml) and 50 μl of epitope II PSA mAb (60 ng/ml) were added to various concentrations (25, 10, or 4 ng/ml) of PSA and incubated for 4 hours. The mixture was added to the microtiter plate well containing epitope I PSA mAb and incubated for 4 hours. The entire mixture was transferred to a microtiter plate of epitope II PSA mAb and incubated for 4 hours. The plates were washed and goat anti PSA at 2 μg/ml was added, and incubated for 4 hours. The plates were washed again and rabbit anti-goat Ig horseradish peroxidase (1:5000) was added and incubated overnight at 4° C. followed by OPD substrate development for 30 minutes. The response in each well was measured photometrically with the Spectra Max 340 (Molecular Devices).

In this example, PSA antigen bound with 15 ng/ml of the incubation antibody to PSA epitope I, and with 60 ng/ml of the incubation antibody to PSA epitope II, was detected at a concentration of 4 ng/ml PSA in the first reaction zone containing 10 µg/ml of PSA epitope I capture antibody. Similar to Example 3 above, this demonstrates that the concentration threshold for PSA is 4 ng/ml when the reagent zone includes 15 ng/ml of PSA epitope I incubation antibody. Because the antibody to epitope I of PSA binds to PSA independently of the antibody to PSA epitope II, PSA antigen bound to epitope I antibody remained capable of binding to the epitope II antibody in the reaction zone. PSA antigen bound with 15 ng/ml of the incubation antibody to PSA epitope I, and 60 ng/ml of the incubation antibody to PSA epitope II, was detectable at a PSA concentration of about 25 ng/ml in the second reaction zone containing 10 µg/ml of the capture antibody to PSA epitope II. This indicates that the concentration threshold for PSA is 25 ng/ml when the reagent zone includes 60 ng/ml of the PSA epitope II incubation antibody.

By way of example and based on the results of these experiments, to make a first reaction zone containing PSA epitope I capture antibody have a concentration threshold of 4 ng/ml, the reagent zone includes 15 ng/ml of PSA epitope I incubation antibody. Similarly, to make a second reaction zone containing PSA epitope II capture antibody have a concentration threshold of 25 ng/ml, the reagent zone includes 60 ng/ml of PSA epitope II incubation antibody. Referring to this example, if the concentration of PSA in a biological sample was 30 ng/ml, a positive staining would appear in both reaction zones because the PSA concentration exceeds the concentration threshold for the first reaction zone (4 ng/ml) and the concentration threshold for the second reaction zone (25 ng/ml). Similarly, if the PSA concentration was 15 ng/ml, only the first reaction zone containing the PSA epitope I capture antibody would be stained because the PSA concentration is greater than the concentration threshold of the first reaction zone (4 ng/ml) but is less than the concentration threshold for the second reaction zone (25 ng/ml). Likewise, if the PSA concentration was 2 ng/ml, neither reaction zone would be stained because the PSA concentration is less than the concentration threshold for the first reaction zone (4 ng/ml) and the concentration threshold for the second reaction zone (25 ng/ml).

Thus, by way of the invention, an improved immunoassay device and methods are provided that reveal more quantitative information about antigen concentrations in a sample than conventional immunochromatography assays, but reduce the expense, time, and training of conventional quantitative immunoassay systems.

As will be apparent to those skilled in the art to which the invention pertains, the present invention may be embodied in forms other than those specifically disclosed above without departing from the spirit or essential characteristics of the invention. The particular embodiments of the invention described above, are, therefore, to be considered as illustrative and not restrictive. The scope of the present invention is as set forth in the appended claims rather than being limited to the examples contained in the foregoing description.

I claim:

1. A method for determining a quantity of an antigen in a biological sample from a subject, comprising exposing the sample to a solid support device having:

(a) a first reaction zone which contains a predetermined amount of a first capture antibody bound to the solid support, that binds to a first epitope of the antigen;
   (b) a second reaction zone which contains a predetermined amount of a second capture antibody bound to the solid support, that binds to a second epitope of the antigen, said first and second reaction zones located so as to be sequentially exposed to the sample; and
   (c) a reagent zone containing predetermined concentrations of the first and second capture antibodies as incubation antibodies, reactive with the first and second antigen epitopes, and a predetermined concentration of a third antibody bound to a detectable label, said third antibody binding a third epitope of the antigen, wherein the sample is first contacted with the reagent zone of (c) and subsequently either the reaction zones of (a) and (b); wherein the incubation, capture and detection antibodies determine the quantity of the antigen so detected; and wherein a detectable signal in each of the detection zones is directly related to the quantity of antigen so detected.

2. The method of claim 1, further comprising at least one additional reaction zone coupled with a predetermined amount of at least one additional capture antibody that correspondingly binds to at least one additional epitope of the antigen, said additional capture antibody also present as an incubation antibody at a predetermined concentration in the reagent zone.

3. The method of claim 1, wherein said antigen is Prostate Specific Antigen (PSA).

4. The method of claim 1, wherein the detectable label is selected from the group consisting of colored particles, chromophores, radioisotopes and enzymes.

5. The method of claim 1, wherein the quantity of the antigen so detected is 1 ng/ml, 2 ng/ml, 4 nglml, 10 ng/ml, 20 ng/ml or 25 ng/ml.

6. The method of claim 1, wherein the quantity of the antigen so detected is between 1 ng/ml to 1 µg/ml or 1 ng/ml to 25 ng/ml.

7. An assay device for determining a quantity of an antigen in a biological sample from a subject, comprising a solid support having:

(a) a first reaction zone which contains a predetermined amount of a first capture antibody bound to the solid support, that binds to a first epitope of the antigen;
   (b) a second reaction zone which contains a predetermined amount of a second capture antibody bound to the solid support, that binds to a second epitope of the antigen, said first and second reaction zones located so as to be sequentially exposed to the sample; and
   (c) a reagent zone containing predetermined concentrations of the first and second capture antibodies as incubation antibodies, reactive with the first and second antigen epitopes, and a predetermined concentration of a third antibody bound to a detectable label, said third antibody binding a third epitope of the antigen, wherein the sample is first contacted with the reagent zone of (c) and subsequently either the reaction zones of (a) and (b); wherein the incubation, capture and detection antibodies determine the quantity of the antigen so detected; and wherein a detectable signal in each of the detection zones is directly related to the quantity of antigen so detected.

* * * * *